US009561028B1

(12) United States Patent
Fan

(10) Patent No.: US 9,561,028 B1
(45) Date of Patent: Feb. 7, 2017

(54) AUTOMATIC LAPAROSCOPIC KNOT TYING INSTRUMENT

(71) Applicant: Peter Fan, Saddle River, NJ (US)

(72) Inventor: Peter Fan, Saddle River, NJ (US)

( * ) Notice: Subject to any disclaimer, the term of this patent is extended or adjusted under 35 U.S.C. 154(b) by 0 days.

(21) Appl. No.: 14/973,858

(22) Filed: Dec. 18, 2015

(51) Int. Cl.
   *A61B 17/04* (2006.01)
   *A61B 17/02* (2006.01)
   *A61B 17/06* (2006.01)

(52) U.S. Cl.
   CPC ....... *A61B 17/0469* (2013.01); *A61B 17/0482* (2013.01); *A61B 17/0483* (2013.01); *A61B 17/0485* (2013.01); *A61B 2017/0474* (2013.01); *A61B 2017/0496* (2013.01)

(58) Field of Classification Search
   CPC ............ A61B 17/0469; A61B 17/0482; A61B 17/0483; A61B 17/0485; A61B 2017/0474; A61B 2017/0496
   See application file for complete search history.

(56) References Cited

U.S. PATENT DOCUMENTS

| | | | | |
|---|---|---|---|---|
| 5,320,629 A | * | 6/1994 | Noda .................. | A61B 17/0469 606/113 |
| 5,501,690 A | * | 3/1996 | Measamer ......... | A61B 17/0469 606/144 |
| 5,520,702 A | * | 5/1996 | Sauer ................. | A61B 17/0469 29/751 |

(Continued)

Primary Examiner — Matthew F Desanto

(57) ABSTRACT

In laparoscopic surgery, tying of knots is not easy, as it involves the use of long handled graspers and the necessity to pass one end of the suture ligature around the opposite half of the suture, with release and re-grab of the passing end of the suture. The present invention avoids the "passing with the release and re-grab", and makes the tying easier, faster and automatic. It conforms to the general size and shape of a standard laparoscopic instrument. The handle is pistol shaped with two control triggers, one for grasping and the other for rotating. The sheath is elongated and tubular, containing two control rods. The tip is bullet shaped, containing three operating mechanisms, one for grasping the leading end of a suture, a second for trapping the opposite half of the same suture, a third for rotating the grasped end of the suture 360 degrees around the trapped portion, thus forming a knot.

The trapping mechanism uses an axle with a hollow center and an open-ended side slot. The other members of the rotating and trapping mechanisms have these same features, which allow the suture to enter and exit the hollow center. Grasping is performed by a miniature grasper, which has no handle or shaft, with its entire body contained within a part that rotates, called the rotator. Rotation is generated by a slider-crank mechanism which converts linear motion to rotary motion, and avoids the dead centers with a patented L-shaped connecting rod and deflecting pillars (U.S. Pat. No. 9,194,468). The rotation is then transmitted through two modified spur gears to the rotator, and hence also to the miniature grasper. The rotator represents a short sagittal segment removed from the tip, modified to rotate and to contain the miniature grasper, and then replaced in position. To enable the grasper to rotate, there is an intentional discontinuity in its controlling rod, but control from the handle is maintained by the interposition of a semi-open ball and socket joint in the rod.

2 Claims, 24 Drawing Sheets

(56) References Cited

U.S. PATENT DOCUMENTS

| | | | | |
|---|---|---|---|---|
| 5,527,322 A * | 6/1996 | Klein | ................ | A61B 17/0057 |
| | | | | 112/169 |
| 5,549,618 A * | 8/1996 | Fleenor | .............. | A61B 17/0469 |
| | | | | 112/169 |
| 5,702,407 A * | 12/1997 | Kaji | .................. | A61B 17/0469 |
| | | | | 606/139 |
| 5,797,928 A * | 8/1998 | Kogasaka | .......... | A61B 17/0469 |
| | | | | 606/139 |
| 6,716,224 B2 * | 4/2004 | Singhatat | .......... | A61B 17/0469 |
| | | | | 289/17 |
| 7,833,237 B2 * | 11/2010 | Sauer | ................ | A61B 17/0467 |
| | | | | 606/139 |
| 8,038,689 B2 * | 10/2011 | Kawai | ................ | A61B 17/0469 |
| | | | | 606/139 |
| 9,107,657 B2 * | 8/2015 | Uchida | .............. | A61B 17/0469 |
| 9,194,468 B1 * | 11/2015 | Fan | ......................... | F16H 21/28 |
| 9,427,226 B2 * | 8/2016 | Martin | .............. | A61B 17/0469 |
| 2014/0276979 A1 * | 9/2014 | Sauer | ................ | A61B 17/0469 |
| | | | | 606/144 |

* cited by examiner

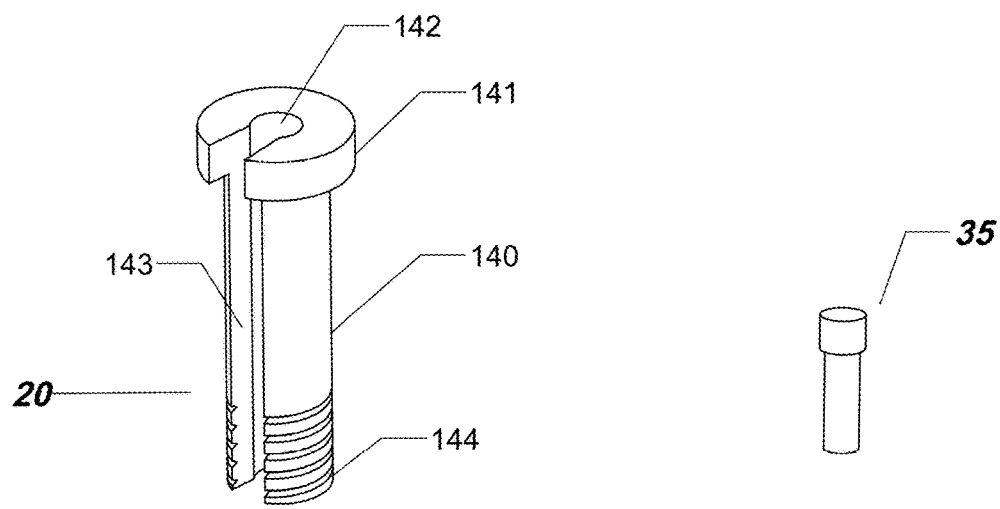
*Fig. 26*  *Fig. 27*
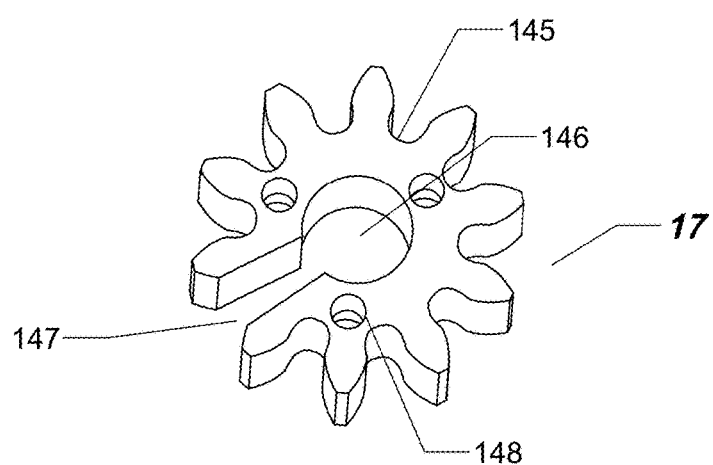
*Fig. 28*

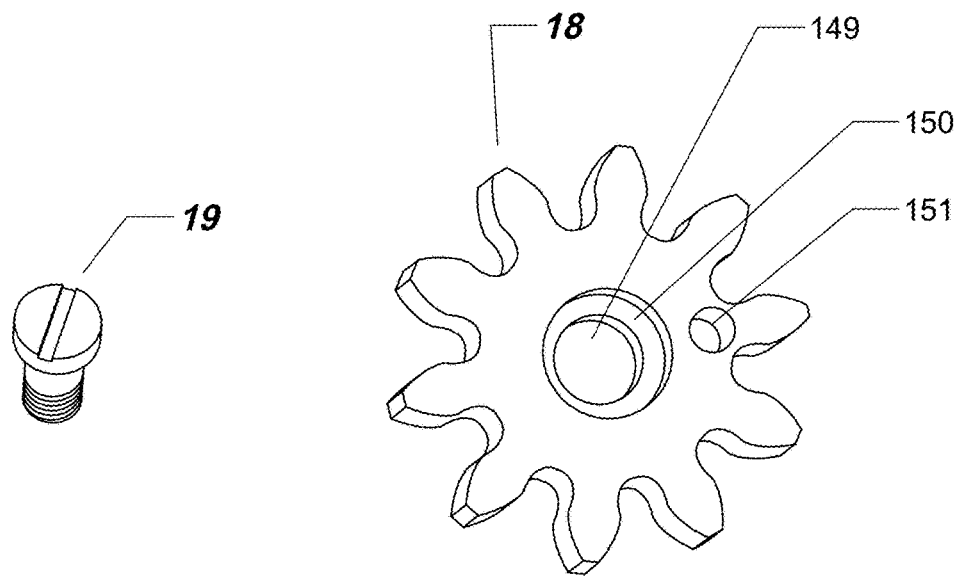
Fig. 29     Fig. 30
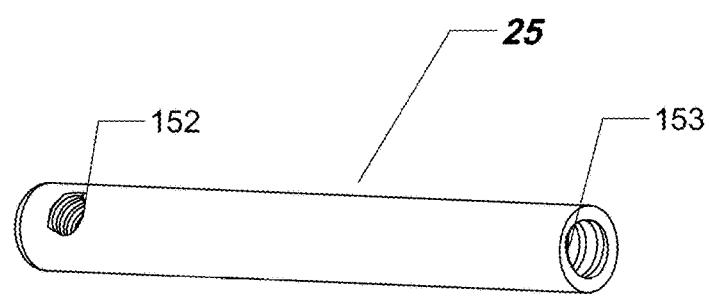
Fig. 31

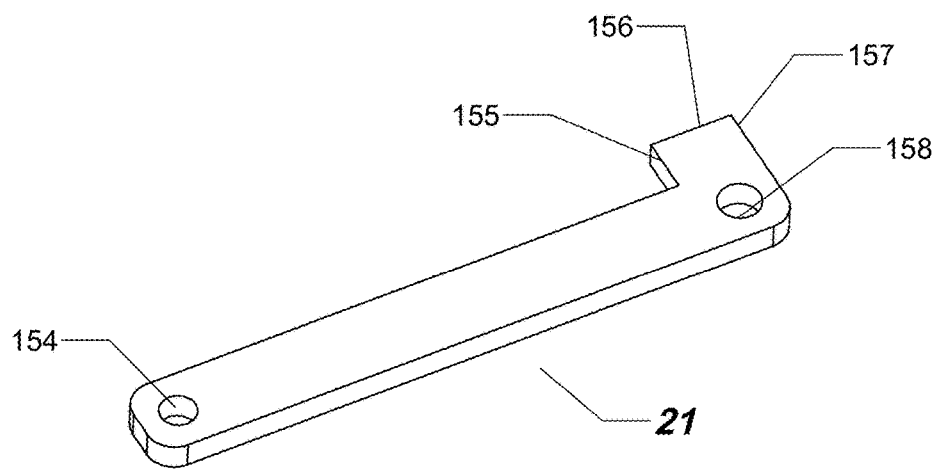
Fig. 32  PRIOR ART
Fig. 33
Fig. 34

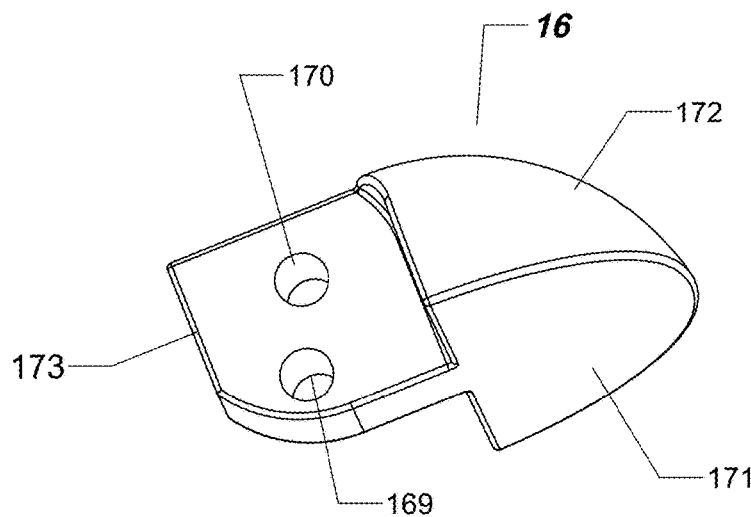
*Fig. 40*
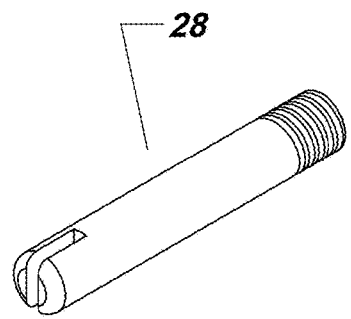 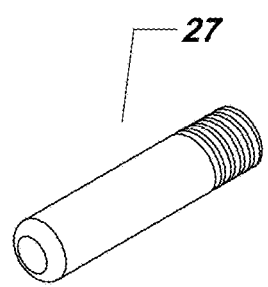
*Fig. 41*  *Fig. 42*

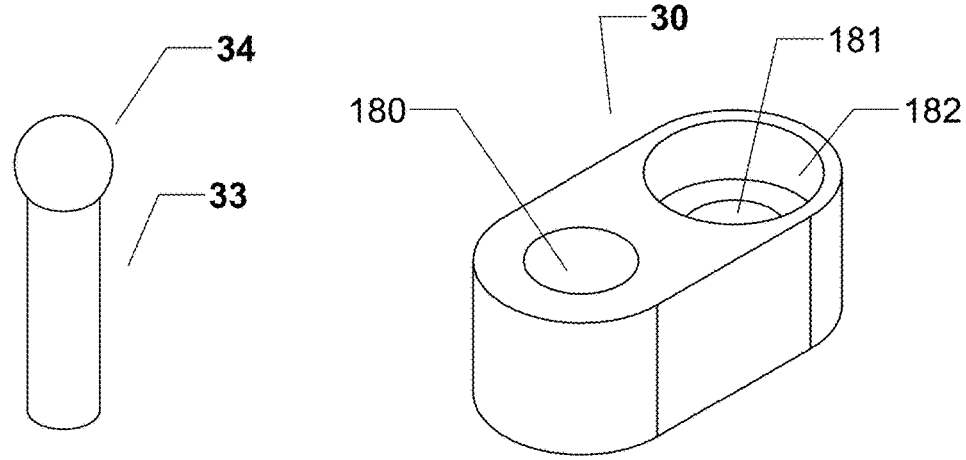
*Fig. 48*        *Fig. 49*
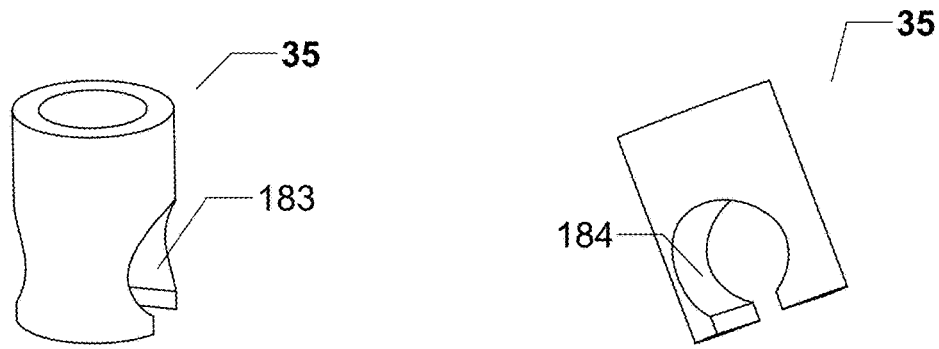
*Fig. 50*        *Fig. 51*

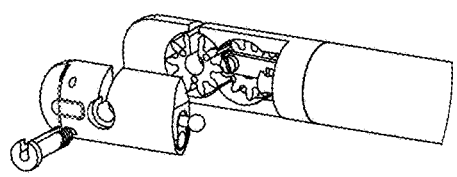
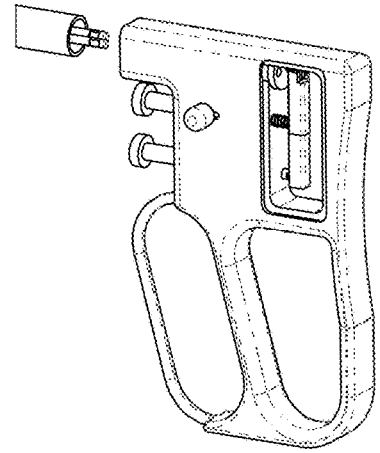
Fig. 56               Fig. 57
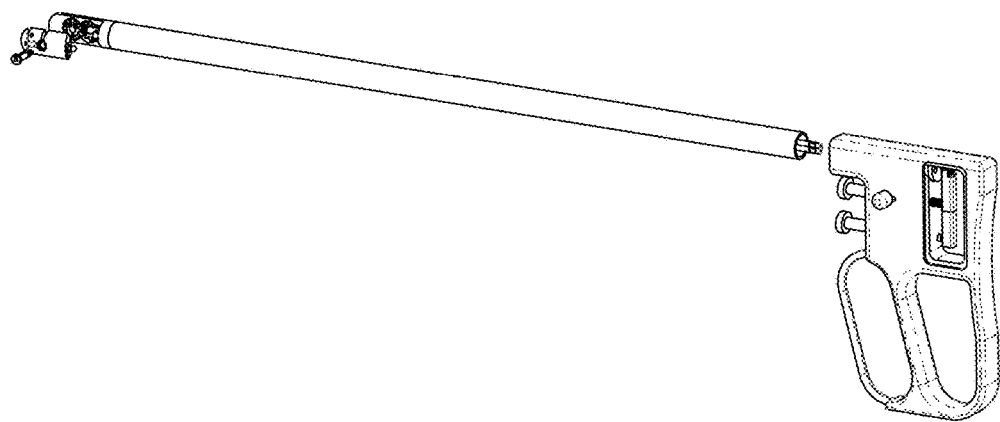
Fig. 58

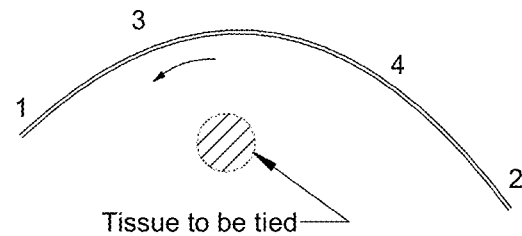
*Fig. 59*     PRIOR ART
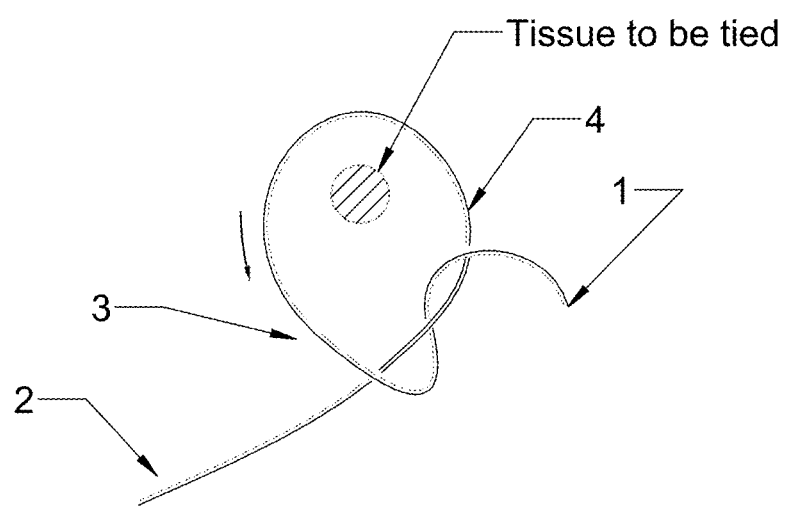
*Fig. 60*     PRIOR ART

AUTOMATIC LAPAROSCOPIC KNOT TYING INSTRUMENT

FIELD OF THE INVENTION

A laparoscopic surgical instrument for intra-corporeal knot tying which makes the throw automatically on a free strand of suture ligature, and avoids using the pass or the loop, or having one end of the suture attached to a needle, disc or cartridge It may be adapted for use in open surgery in deep cavities where the fingers cannot reach, or for use by the robot.

BACKGROUND OF THE INVENTION

Tying of knots is essential in any kind of surgery. It is relatively easy in open surgery, but is difficult in laparoscopic surgery. The current art of laparoscopic knot tying employs either the extra-corporeal method, involving tying the knot by hand outside the body and pushing the knot inside with a knot pusher, or the intra-corporeal method, involving manipulation of the suture with the tips of two laparoscopic graspers, which is cumbersome, and requires considerable skill. Laparoscopic clip appliers, staplers, pre-tied knots and the like are useful substitutes, but cannot totally replace tied knots. Despite considerable prior art, there still is no hand operated instrument that renders laparoscopic intra-corporeal knot tying easier and faster.

In order to describe the tying process, the different parts of the suture ligature need to be given names. As shown in FIG. 59 in the drawings, after the suture ligature has passed around the tissue to be tied, it then presents with a head end (1), a tail end (2), a leading strand (3) and a tail strand (4), There are two basic methods of tying a knot, whether done openly or laparoscopically. One method is making a "throw" which involves passing the head end of the suture around its tail strand. This is quite simple when performed with the fingers as in tying shoe laces. It does however involve a critical step which is the passing or release and re-grab of the head end of the suture, and wrapping it around the tail strand. In laparoscopic surgery this is difficult because the graspers are trapped in the abdominal wall, and the surgeon is limited to using only two laparoscopic graspers, one in each hand. Hence the reason for the present invention.

The second method of tying a knot involves making a loop or loops, which is commonly performed in open surgery by the surgeon making "instrument ties", where he uses a needle holder and wraps the suture several times around it. This can be done laparoscopically but is generally difficult. There are many patents in the prior art that try to make the loop laparoscopically, but none has been commercially successful, and this is not the object of the present invention.

the present invention makes the knot differently and automatically without making the loop, or making the pass. Additionally it ties a knot in a free strand of suture ligature, without having one end of the suture being pre-fixed on to a disc or cartridge. It is therefore different in design and technique compared with other previous similar inventions.

Referring to the prior art, the Christoudias Double Grasper has 3 jaws, with a common middle jaw, and functions as a tissue approximator. Its spring loaded actuators are operated by two push buttons. The Ferzli Double Grasper, has a second pair of jaws positioned more proximally on the main shaft, whose purpose is to anchor one end of the suture prior to twisting it around the shaft of the instrument in order to produce a loop. The Hasson Suture Tying Forceps, is similar to the Ferzli, with 3 finger loops. The orthopedic suture passers are for passing sutures only through hard tissue, and these include the Arthrex Scorpion Suture Passer, and the Arthrex Birdbeak Suture Passer. Some suture passers are for passing sutures through a thickness of soft tissue such as the abdominal wall, and these include the Goretex and the Aesculap. There are devices which "pass the suture-needle" side to side, for inserting sutures into tissues, as well as for tying knots, e.g. the Autosuture's Endo-stitch, and the Japanese Maniceps. Note these only pass the suture needle, not the suture thread per se. There have been devices that attempt to "automatically" tie a knot, such as Jerrigan's experimental rotating slotted disc designed for robotic endo-cardiac surgery, but it was abandoned because of the requirement for a cartridge. There have been many devices that help to "create a loop", with each functioning differently—(a) Kitano's grasper with the rotating sleeve, Japanese, (b) Donald Murphy's grasper with the extra horn, Australian, (c) Grice's sleeve catching instrument, (d) Bagnato & Wilson's device which simulates the radiological pig-tail catheter, with a preformed loop built into the tip of the catheter, which is deformable and purportedly a loop former, but it is difficult to manufacture and apply, and has not yet been reduced to practice, (e) Ferzli's double grasper, which anchors one end of the suture, as described above. There have been devices using a "pre-formed knot", (1) Ethicon's Endo-Loop, (2) the Duraknot, (3) LSI's device, (4) Pare's pre-tied knot, all of which do not help to tie knots.

Past inventions related to intra-corporeal laparoscopic knot tying fail to address the basic problem of "how to make the throw". They usually offer various alternatives, such as making multiple loops, similar to fishing knots, using pre-tied knots, knot pushers, suture clips, cinchers, tissue fasteners, anchors, stapling devices, etc. The present invention however will assist in manual intra-corporeal knot tying, and will help to produce the knot automatically.

U.S. PATENT DOCUMENTS

| | | | | |
|---|---|---|---|---|
| 1. | 3,834,395 | Sept. 10, 1974 | Manuel Santos | 128/326 |
| 2. | 5,201,759 | Apr. 13, 1993 | George Ferzli. | 606/139 |
| 3. | 5,217,471 | Jun. 8, 1993 | Stephen Burkhart | 606/148 |
| 4. | 5,234,443 | Aug. 10, 1993 | Phan & Stoller | 606/148 |
| 5. | 5,250,054 | Oct. 5, 1993 | Lehmann Li | 606/148 |
| 6. | 5,281,236 | Jan. 25,1994 | Bagnato et al. | 606/139 |
| 7. | 5,312,423 | May 17, 1994 | Rosenbluth & Brenneman | 606/148 |
| 8. | 5,395,382 | Mar. 7, 1995 | DiGiovanni et al. | 606/148 |
| 9. | 5,437,682 | Aug. 1, 1995 | Drew Grice | 606/148 |
| 10. | 5,423,836 | Jun. 13, 1995 | Scott Brown | 606/148 |
| 11. | 5,439,467 | Aug. 8, 1995 | Theodore Benderev, et al. | 606/139 |
| 12. | 5,480,406 | Jan. 2, 1996 | Nolan et al. | 606/139 |
| 13. | 5,728,109 | Mar. 17, 1998 | Schulze et al. | 606/148 |
| 14. | 5,810,852 | Sept. 22, 1998 | Greenberg et al. | 606/148 |
| 15. | 5,814,054 | Spet. 29, 1998 | Kortenbach et al. | 606/139 |
| 16. | 5,846,254 | Dec. 8, 1998 | Schulze et al. | 606/228 |
| 17. | 6,051,006 | Apr. 18, 2000 | Shluzas & Sikora | 606/148 |
| 18. | 6,086,601 | Jul. 1, 2000 | InBae Yoon | 606/148 |
| 19. | 6,221,084 | Apr. 24, 2001 | R. Fleenor, Pare Surgical | 606/148 |
| 20. | 6,432,118 | Aug. 13, 2002 | Mollenhauer & Kucklick | 606/148 |
| 21. | 6,716,224 | Apr. 26, 2004 | Singhatat | 606/148 |
| 22. | 2009/0228025 | Sept. 10, 2009 | Steven Benson | 606/144 |
| 23. | 2010/0016883 | Jan. 21, 2010 | George Christoudias | 606/205 |
| 23. | 5,312,423 | May 17, 1994 | Rosenbluth et al. | 606/148 |
| 25 | 8,512,362 | Aug. 20, 2013 | Ewers et al. | 606/158 |

OTHER PUBLICATIONS

1. Endo-stitch—Autosuture—Manufacturer's item #173016.

2. Maniceps—Japanese suturing device, similar to Endostitch.
3. A Laparoscopic Device for Minimally Invasive Cardiac Surg (rotating slotted disc). Shaphan Jernigan, et. al.—European J. of Cardio-thoracic Surgery, Vol. 37, p.626-630. March 2010.
4. Knot Tying Intra-corporeally, with newly designed Forceps. (sliding sleeve).
5. Kitano et. al.—J. of Minimal Invasive Therapy & Allied Tech, 1996. 5: 27-28.
6. Endoscopic Knot Tying Made Easier—(one jaw with extra bump).
7. Donald Murphy—ANZ J. Surg. 1995. 65, 507-509.
8. The Excalibur Suturing Needle Holder—(jaw with prominent heel, helps looping)
9. Uchida et. al. Surgical Endoscopy—vol. 3, 531-532
10. Alijizawi laparoscopic auto-knot device—(two dissolving balls).
11. A New Reusable Instrument designed for simple and secure knot tying in laparoscopic surgery. S. S. Miller 1996 Surg. Endos 10: 940-941 (pointed canula).
12. The Nobel Automatic Laparoscopic Knotting and Suturing Device. Mishra et. al. World Laparoscopy Hospital, India. (a knot pusher)
13. Automated Knot Tying for Fixation in Minimally Invasive Robot Assisted Cardiac Surgery. March 9(1):105-12.
14. Kuniholm & Buckner—J. Biomed Eng. November 2005, Vol. 127, 1001-8. JSLS. Jan. 17, 2005.
15. M I Frecke—Laparoscopic multifunctional instruments: design and testing. Endosc Surg Allied Technol. 1994 December; 2(6):318-9.
16. G. Berci—Multifunctional laparoscopic Instruments.
17. http://www.ligasure.com/ligasure/pages.aspx?page=Products/Laparoscopi
18. http://www.freepatentsonline.com/y2010/0063437.
19. http//www.ncbi.nlm.nih.gov/pubmed/15791983 Multifunctional Laparoscopic Instruments.
SUGGESTED U.S. CLASSIFICATION: 606/139, 144, 145, 148.
SUGGESTED INTERNATIONAL CLASSIFICATION: A61B 17/00, 04, 28.
FIELD OF SEARCH: 606/139, 144, 145, 147, 148, 150, 151, 127, 128, 606/167, 168, 170, 174, 182, 185, 205, 207, 210, 211.
RELATED PRIOR PATENT: U.S. Pat. No. 9,194,468.

SUMMARY OF THE INVENTION

In laparoscopic surgery, the advent of laparoscopic clips and staples has been a great blessing to surgeons, but cannot totally replace the use of tied knots, which when performed intra-corporeally, is technically difficult, but still necessary. The instrument presented here is intended to facilitate intra-corporeal laparoscopic knot tying with a free strand of suture ligature. It conforms to the customary shape and size of a laparoscopic instrument, with an elongated round sheath, a pistol shaped handle at the proximal end, and a bullet shaped tip at the distal end. Three operating mechanisms are incorporated in the tip: firstly, a grasping mechanism involving the use of a mini-grasper, which is small enough to be contained inside an element that rotates, called the rotator; secondly, a trapping mechanism involving the use of a slotted hollow axle which is an axle with a hollow center, and also involving the use of an open-ended slot on the side of each member of the rotating mechanism, which enables a portion of the tail end of the suture to be trapped within the hollow center, whilst the rotation takes place; thirdly, a finger activated rotation system, which uses a slider-crank mechanism to convert linear into rotary motion, and uses a patented L-shaped connecting rod to avoid dead centers, and also uses a slotted driven spur gear to transmit the rotation to the slotted rotator, which houses the mini-grasper.

Other characteristics •of this instrument include: (1) manipulating both ends of the same suture with the same instrument, (2) being hand operated, avoiding the use of electricity or battery, (3) may be used with a robot, (4) may be used to tie knots in any deep and narrow cavity where the surgeon's fingers cannot reach, (5) allowing the surgeon to tie a knot laparoscopically and automatically, using only his own two hands, without need for help from an assistant.

BRIEF DESCRIPTION OF THE DRAWINGS

FIG. 26 is a perspective view of the slotted hollow axle.

FIG. 27 shows one of the 3 pins that holds the slotted driven spur gear.

FIG. 28 is a picture of the driven slotted spur gear.

FIG. 29 is a picture of the shoulder screw that holds the driving spur gear.

FIG. 30 is a picture of the driving spur gear.

FIG. 31 is a perspective view of the gear rod.

FIG. 32 is a perspective view of the L-shaped connecting rod.

FIGS. 33 and 34 show the shoulder screws used at the ends of the L-rod.

FIG. 40 is a perspective view of the upper jaw.

FIG. 41 is a view of the pin that acts as the fulcrum for the upper jaw;

FIG. 42 is a view of the pin that moves the upper jaw.

FIG. 48 is a picture of the ball with the stem.

FIG. 49 is a perspective view of the oval plate located at the top of the rotator.

FIG. 50 and FIG. 51 are perspective views of the socket that contains the ball.

FIGS. 56, 57 and 58 show the order of assembly of the major sub-assemblies of the device.

FIG. 59 is diagram indicating the names of the different parts of a suture ligature.

FIG. 60 is diagram showing how a standard throw is formed.

DETAILED DESCRIPTION OF THE PREFERRED EMBODIMENT

Figure 1:
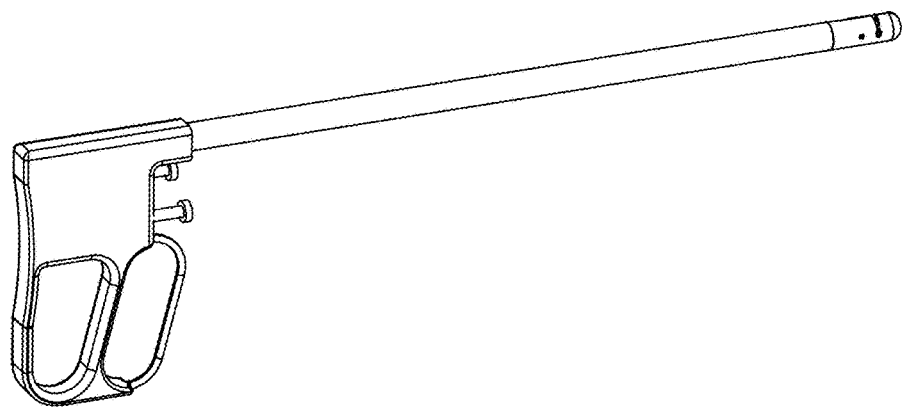
FIG. 1 is perspective view of the entire device from the right side.
Figure 2:
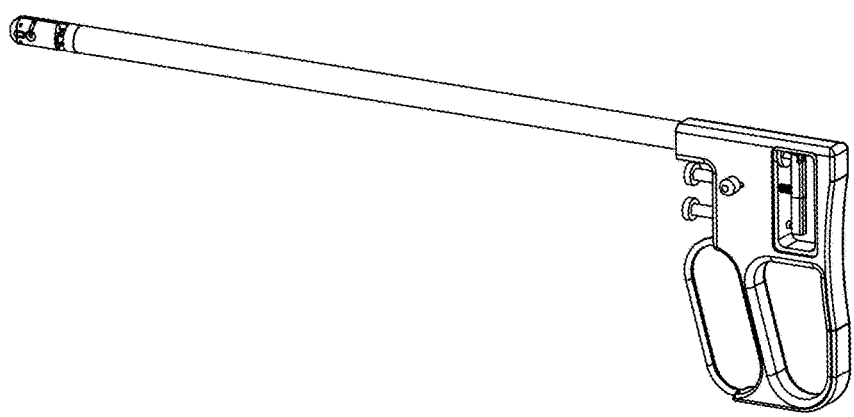
FIG. 2 is the entire device from the left side.
Figure 3:
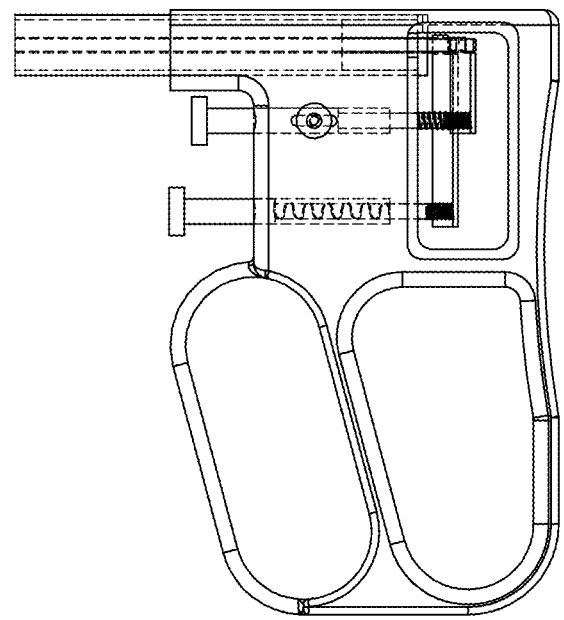
FIG. 3 is a transparent view of the left side of the handle.
Figure 4:
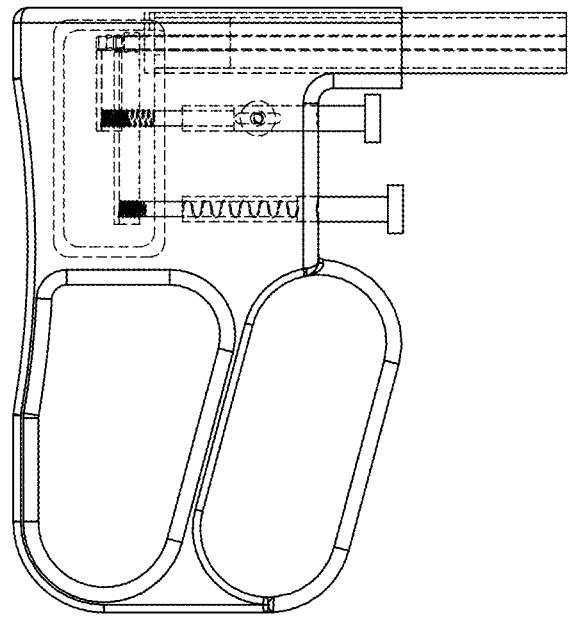
FIG. 4 is the same of the right side of the handle, showing the arrangement of the triggers.
Figure 5:
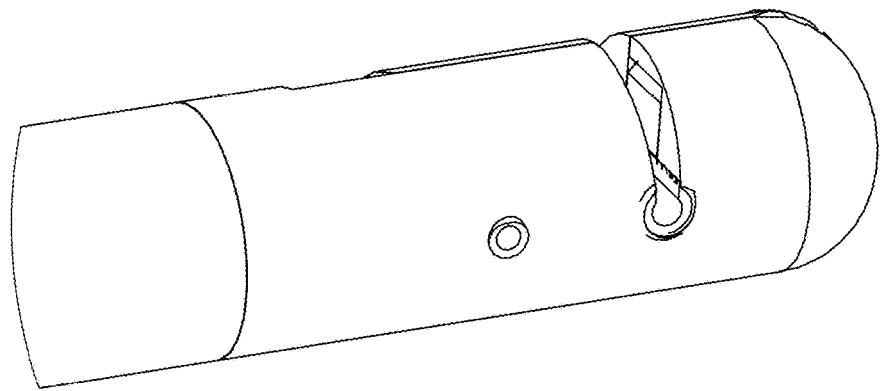
FIG. 5 is a perspective view of the right side of the tip of the instrument.
Figure 6:
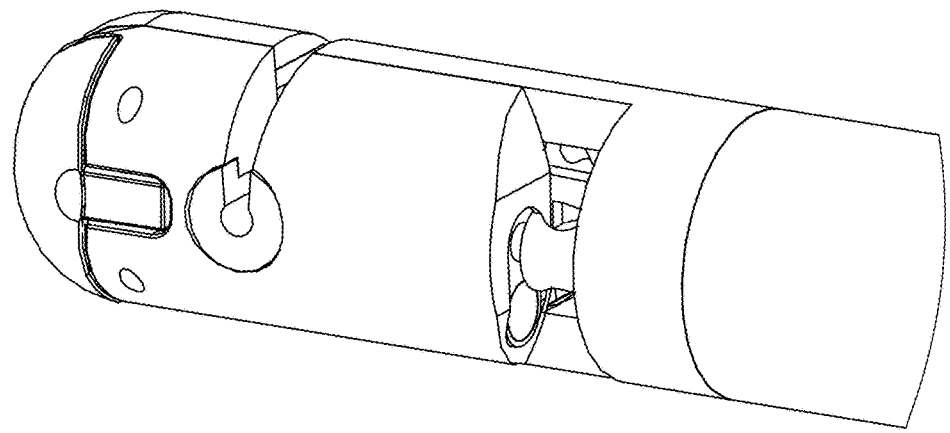
FIG. 6 is the left side of the tip, showing the different appearances of the two sides.

The invention here deploys the following steps in tying a knot: First, the head end of the strand is grasped by a miniature grasper, FIG. 35. Second, the tail strand is temporarily trapped and controlled inside a slotted tubular structure, part 20, FIG. 26.

Third, the miniature grasper which is holding the head end of the suture, is made to rotate 360 degrees around the trapped tail strand, which subsequently escapes from the entrapment, resulting in a tie. In essence, the process requires the tail strand to be temporarily constrained in space, whilst the head end of the suture rotates around it.

The trapping in this device is accomplished by using a slotted hollow axle, part 20, FIG. 26, which is an axle with a hollow center, and also a narrow slot along its entire side. The opening of the slot, 143 allows the tail strand to enter into the hollow space in the center of the axle, 142 and subsequently to escape from it.

In order for the rotation of the head end of the suture to occur whilst the tail strand is trapped, the hollow center and the open side slot are also required in all the other components of the rotation system: the base of the tip, 14, to which the slotted hollow axle is attached, the driven spur gear 17, and the rotator 15, which bears the mini-grasper. This arrangement is necessary for the temporary entrapment and subsequent escape of the tail strand of the suture, as well as the rotation of the rotator. To function well, the slots in all these 4 components must line up precisely during trapping and release of the tail strand of the suture, and at rest, and at the end of a 360 degree rotation.

The crossing-over of the head strand over the tail strand comes about naturally because the strand that is trapped lies at 90 degrees from the strand that rotates.

Rotation is provided by a hand operated slider-crank mechanism that converts the linear motion of a finger pull into a rotational motion, which is then transmitted through the two spur gears to a rotator. The rotator 15 is bonded to the slotted driven spur gear 17, and both have a hollow center and an open slot, like the slotted hollow axle. Both rotate as a unit upon the stationary slotted hollow axle 20, and the minigrasper also rotates with them. The slider-crank mechanism uses an L-shaped connecting rod 21, with two deflecting pillars 134 and 135, to overcome dead centers, which is simpler than using other means such as auxiliary rods. For a description and an explanation of the L-shaped connecting rod, reference is made to U.S. Pat. No. 9,194,468, by the author. The slider-crank first rotates a driving spur gear 18, then a slotted driven spur gear 17, then a slotted rotator 15, which carries the mini-grasper The source of energy used for the rotation is a manual pull, with the return being performed automatically by a compression spring. The use of this simple mechanism avoids the use of complicated mechanisms or the use of electricity or the battery.

Figure 35:
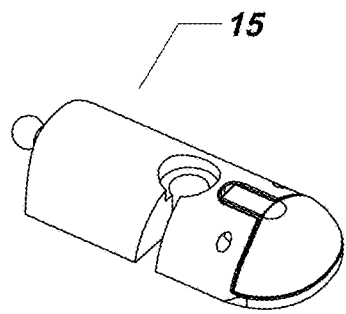
FIG. 35 is a perspective view of the rotator sub-assembly, with the upper jaw closed.
Figure 36:
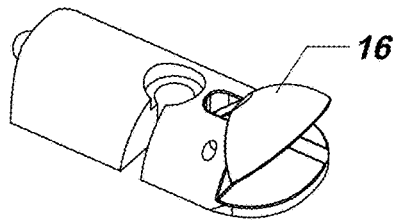
FIG. 36 is the same with the upper jaw open.

The mini-grasper sub-assembly, FIG. 35, 36, 37, is essentially a very short laparoscopic grasper, with one movable jaw, but no handle, and no shaft. The minigrasper is spring loaded, and is housed inside the rotator, which rotates on the slotted hollow axle. The mini-grasper is uniquely small and short, but fully functional. In order for it to rotate, its shaft needs to be separated from the long control rod, and it needs to be small enough to fit inside the rotator. The mini-grasper has only a movable upper jaw 16, which is normally held in a closed position by a compression spring, 32.

To grasp a suture the upper jaw 16 needs to be opened by external pressure on the compression spring 32, exerted from the separated control rod, which is initiated by pushing the thumb knob 9, with the thumb at the handle. A special inter-connecting ball and socket joint, FIG. 48, 49, 50, 51, in the control rod allows the rotator with the mini-grasper, to undergo 360 degree rotation in the sagittal plane of the long axis of the instrument, whilst also permitting the jaws to be remotely controlled from the handle with the push or pull, when the rotator is in the resting neutral position.

After the head end of the suture has been grasped by the mini-grasper, the rotation is activated by the index finger pulling on the trigger 4, which causes the slider-crank mechanism to generate the first half of a rotation. The second half of the rotation is generated by a compression spring, when the trigger 4 is released, and is thus automatic.

After the rotator has completed a full rotation, it may be necessary to pull the suture ends apart to tighten the knot. At this point, because the force of the spring in the mini-grasper holding the suture is of limited strength, additional pressure will need to be applied to the upper jaw to hold on to the suture. This is provided by the trigger 3, also operated by the index finger, whose additional pull will help to provide additional pressure keeping the jaw tightly closed holding on to the suture. The separated grasper rod is therefore provided with both a push as well as a pull activation. The push activation is provided by the thumb, whilst the pull activation is provided by the compression spring as well as by the index finger. There is no problem in using the index finger for two different activations since the two are not used simultaneously.

Figure 7:
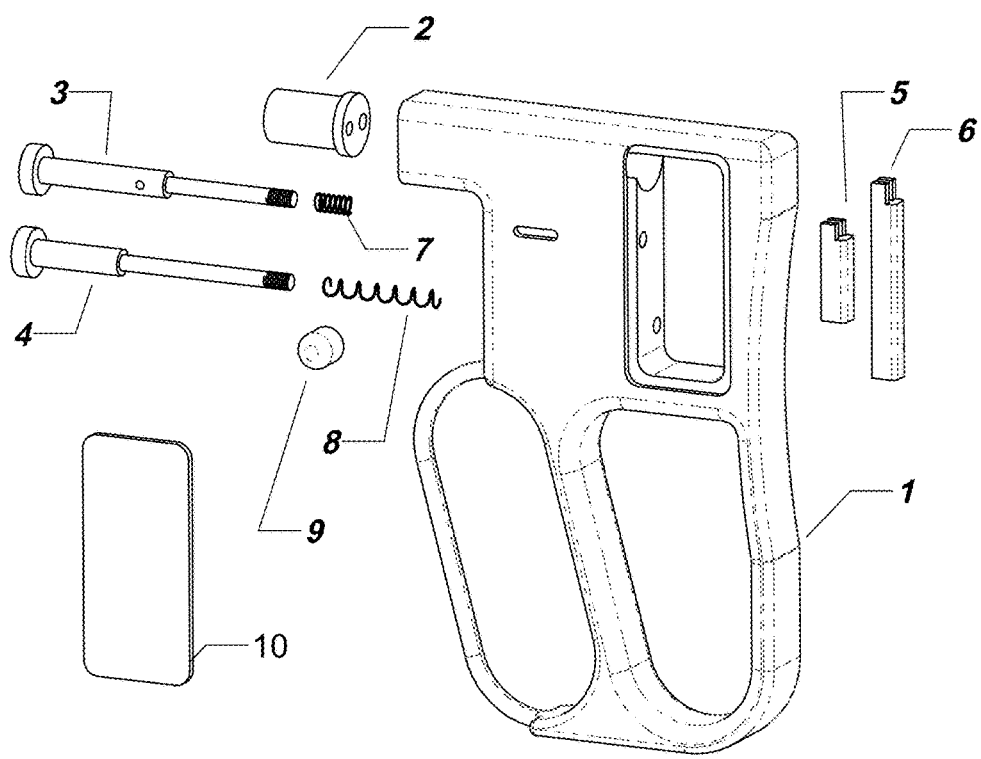
FIG. 7 is an exploded view of the handle-assembly from the left side, showing the numerous components within the handle.

Referring to FIG. 7, the exploded view of the handle sub-assembly, part 1 is a pistol shaped handle which is gripped by the palm and by the middle, ring and little fingers through the loop, whilst freeing the index finger and the thumb for actuation.

The lower trigger is primarily pulled by the index finger. The upper trigger is primarily pushed by the thumb. The return movement on both triggers is performed by compression springs, which are hidden inside the handle. The upper trigger may in addition be pulled by the index finger. The connectors connecting the triggers to the actuating rods are located inside a cavity in the rear of the upper part of the handle.

Part 2 is the proximal spacer, which contains two holes for holding the two rods in place and allows their free passage, and contains a flange to prevent its accidental migration inside the sheath. There is no separate distal spacer which does exist in the rear of the base of the tip. Part 3 is the upper trigger, which is to be pushed forward by the thumb through the push knob, but can also be actively pulled back by the index finger. Part 4 is the lower trigger, which is pulled by the index finger to activate the rotation.

Figure 8:
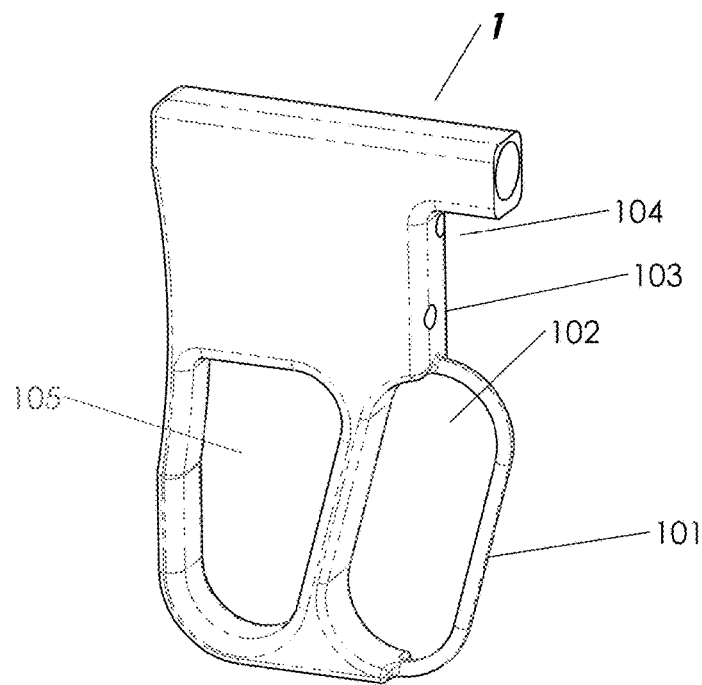
FIG. 8 is a perspective view of the handle from the right side.
Figure 9:
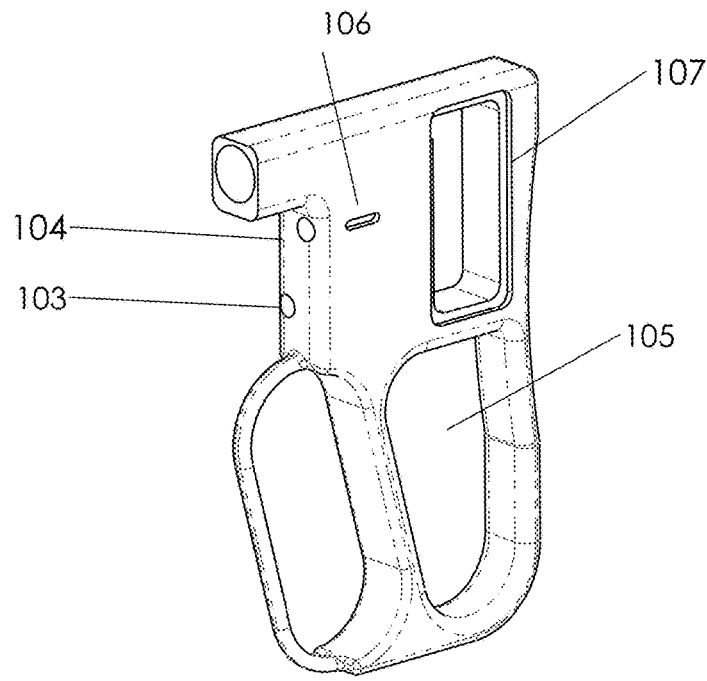
FIG. 9 is the handle from the left side, showing the different features on the two sides.

Both part 3 and part 4 triggers consist of a 9.5 mm diameter button at the outer end, an intermediate 5 mm diameter rod, and an inner 3 mm diameter rod, which screws into the lower end of the respective connectors further described below. Part 5 is the short connector whose upper end receives the flat neck of the proximal end of the push rod, and its lower end receives the upper trigger. Part 6 is the longer connector whose upper end receives the circular neck of the proximal end of the pull rod, and its lower end receives the lower trigger. Part 7 is a short compression spring used with the upper trigger. Part 8 is a long compression spring used with the lower trigger. Part 9 is the thumb push knob which screws into the upper (push/pull) trigger rod used for opening and closing the movable upper jaw of the mini-grasper. Part 10 is the lid for covering up the cavity on the left side of the handle, containing the connectors. FIG. 8 illustrates 101 which refers to the finger loop, 102 refers to the space inside the finger loop. 103 refers to the seating for trigger for the rotary system, whilst 104 refers to the seating of the trigger for the grasper system. 105 is an empty space, to lighten the weight of the handle. FIG. 9 illustrates the handle from the left side, showing different features 106 and 107.

Figure 10:
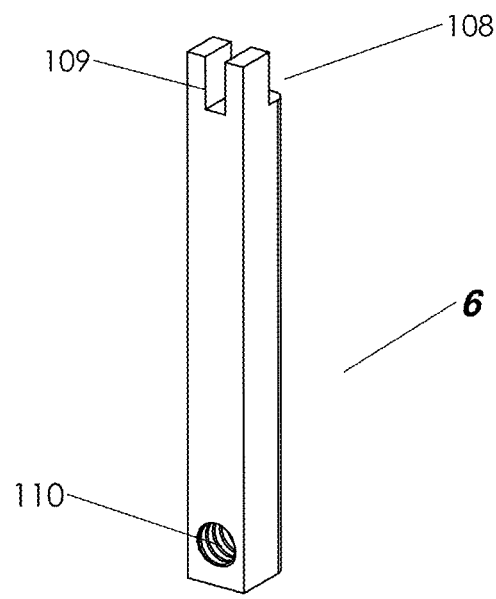
FIG. 10 is a perspective view of the long connector to the trigger of the rotating system and FIG. 11 is a perspective view of the trigger of this system.
Figure 11:
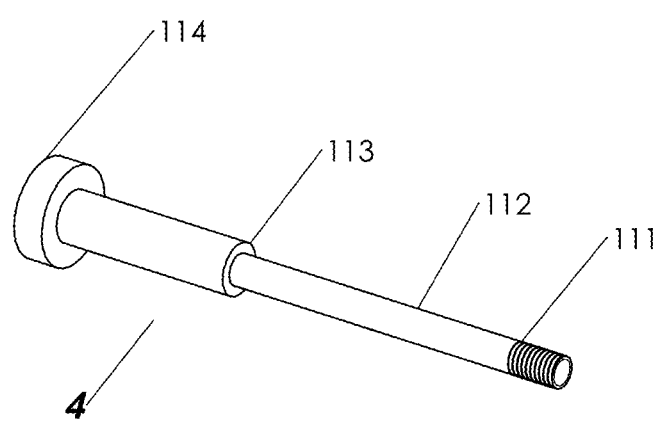
Figure 12:
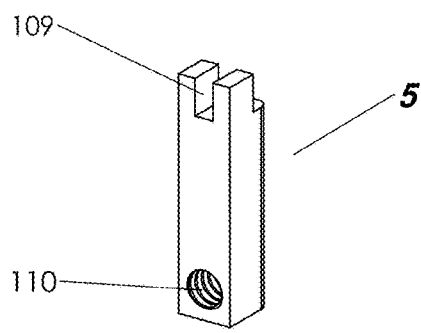
FIG. 12 is a perspective view of the short connector of the grasper rod system.
Figure 13:
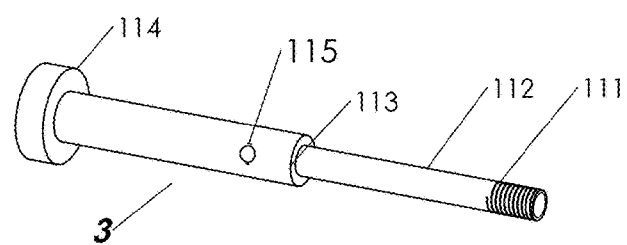
FIG. 13 is a perspective view of the trigger of the grasper rod system.
Figure 14:
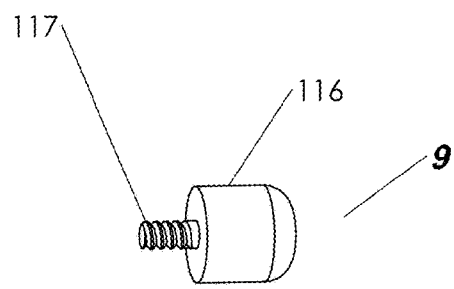
FIG. 14 is a view of the thumb push knob.
Figure 15:
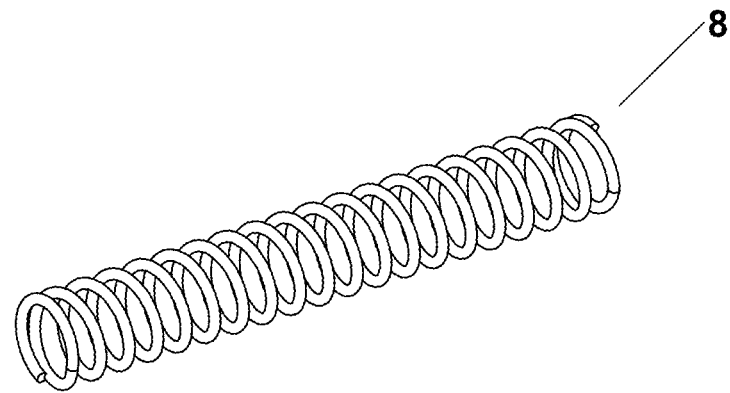
FIG. 15 shows the long compression spring of the trigger of the rotation system.
Figure 16:
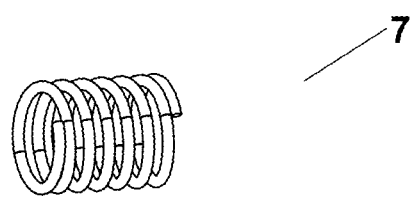
FIG. 16 shows the short compression spring of the trigger of the grasper rod system.
Figure 17:
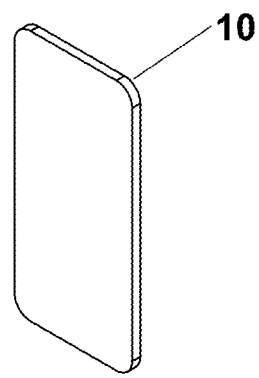
FIG. 17 shows the lid that covers the cavity on the left side the handle.
Figure 18:
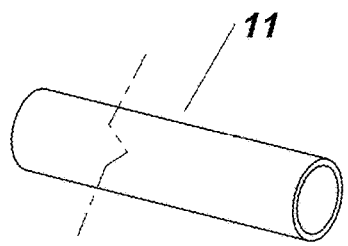
FIG. 18 shows the external sheath that covers the two rods.
Figure 19:
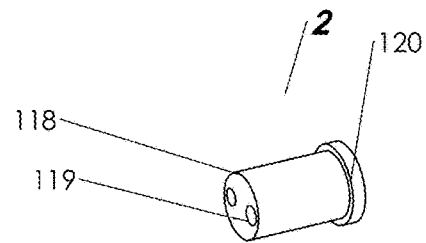
FIG. 19 shows the proximal spacer, which bears two channels.

FIG. 10 is a perspective view of the long connector to the trigger of the rotating system and FIG. 11 is a perspective view of the trigger of this system. 108 shows the seating for the head end of the rod, 109 shows the seating for the flat neck of the rod. 111 is the male threaded end which screws into the hole 110. 112 is the 3 mm diameter portion of the shaft of the trigger, over which the compression spring is installed. 113 is a shoulder stop. 114 is the external button. FIG. 12 is a perspective view of the short connector of the grasper rod system, which is similar to FIG. 10. 109 is the slot that receives the flat neck of the rod. FIG. 13 is a perspective view of the trigger of the grasper rod system, showing 115 which is a female threaded hole, receiving 117 of part 9. FIG. 14 is a view of the thumb lush knob 116 of the grasper rod system. FIG. 15 shows the long compression spring of the trigger of the rotation system; FIG. 16 shows the short compression spring of the trigger of the grasper rod system; and FIG. 17 shows the lid that covers the cavity on the left side the handle. FIG. 18 shows the external sheath that covers the two rods. FIG. 19 shows the proximal spacer, which bears two channels, 118 and 119, for supporting the two rods and keeping them aligned. Its rear flange 120 is to prevent accidental migration into the rear of the sheath.

Figure 20:
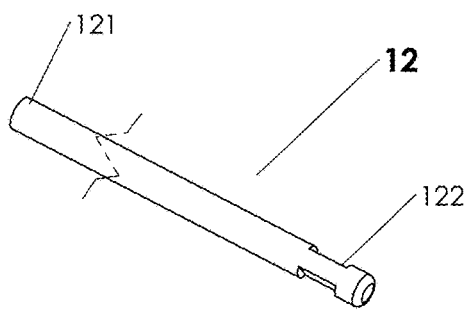
FIG. 20 shows push rod of the grasper system.

FIG. 20 shows part 12, the 2.5 mm push rod of the grasper system, whose proximal end, 122 bears a narrow flat sided neck which mates into the top of the short connector, and helps to prevent accidental rotation of the rod. Its distal end 121 is mated to the socket holding the ball, which is part of a ball and socket joint, which in turn is part of the actuator that moves the upper jaw.

Figure 21:
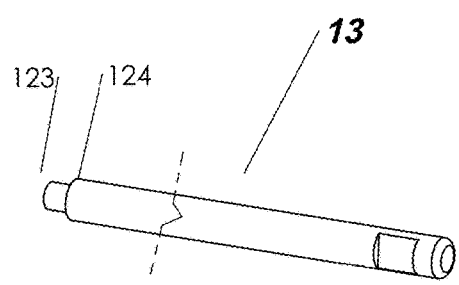
FIG. 21 shows pull rod extension of the rotation system.

FIG. 21 shows part 13, the 3 mm pull rod extension of the rotation system with the narrow flat neck, 124, whose distal end 123, screws into the proximal end of the "gear rod" part 9, and whose proximal end has a round cut out to create a narrow round neck, to mate with the top of the long connector.

Figure 22:
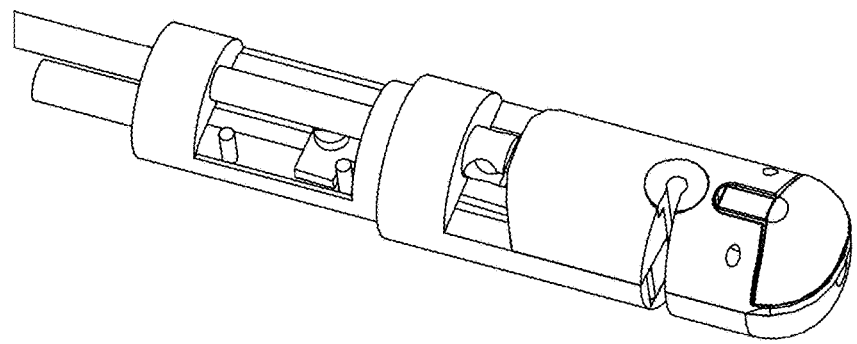
FIG. 22 is a perspective view of the tip-assembly, whilst
Figure 23:
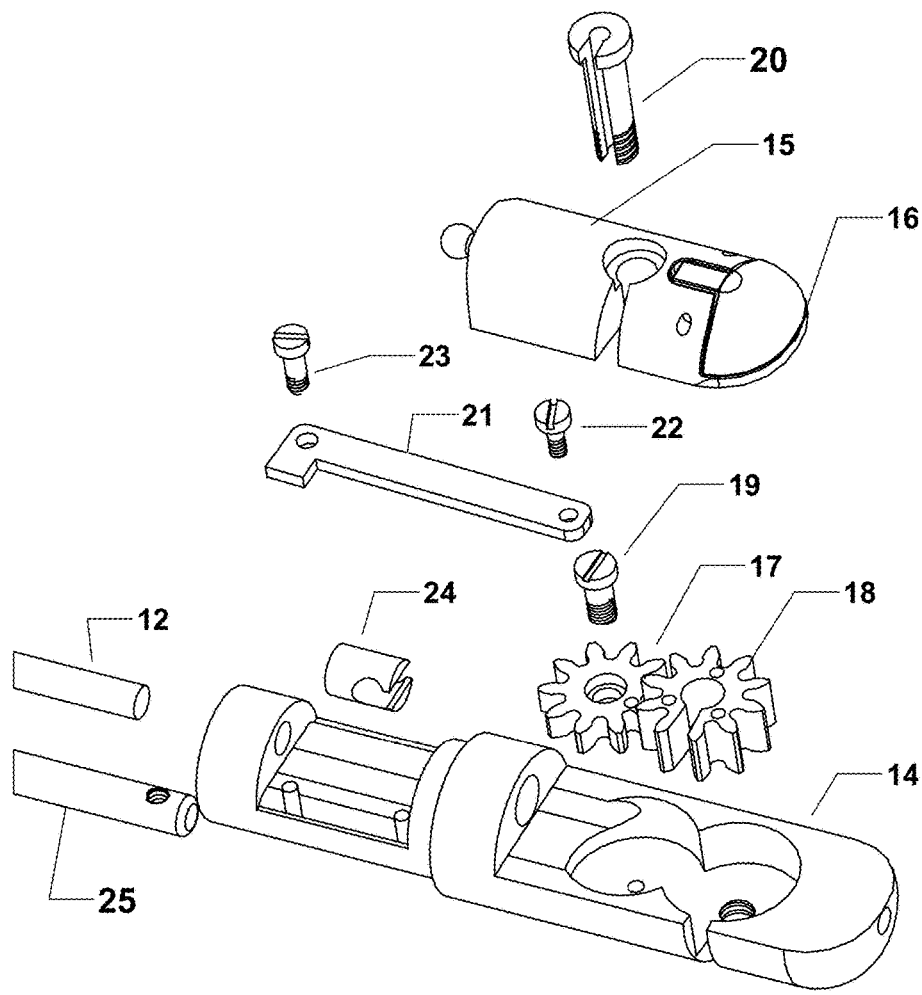
FIG. 23 is an exploded view of the tip-assembly.

FIG. 22 is a perspective view of the tip sub-assembly, whilst FIG. 23 is an exploded view of the same, showing the numerous components. Part 14 is the tip-base, without the rotator, and houses the components of the rotational mechanism, which include the crank-slider, the L-shaped connecting rod, the deflecting pillars, the driving spur gear, and the driven spur sear, and provides the base for fixation of the slotted hollow axle. It also bears a V-shaped slot on its side for guiding the tail end of the suture into the trap. This slot may be located alternately at the very tip of the base. Part 15 is the rotator, which is a complex and crucial body, representing a short sagittal portion of the tip, and participates in each of the trapping, grasping and rotating mechanisms. Part 16 is the movable upper jaw. Part 18 is the driving spur gear, which bears a counter sunk hole in the center for mounting a shoulder screw, and a smaller screw in its periphery for mounting the distal end of the L-shaped connecting rod. It origin is identical to the slotted driven gear, so their teeth can match. Part 17 is the slotted driven spur gear, which is similar to part 18, but has an open slot between two adjacent teeth, allowing access to the hollow space in the center. This is part of the trapping mechanism. Its upper surface is fixed to the underside of the rotator, either by adhesives or by 3 tiny pins, through 3 tiny counter-sunk holes. It is designed intentionally with a small number of teeth, in order to create a wide enough slot between two adjacent teeth, for the suture to pass through. The gap created between two adjacent teeth on the other hand must not damage the teeth. Part 19 is the shoulder screw for mounting the driving spur gear. Part 20 is the slotted hollow axle, which bears a male thread at one end, a retaining flange at the other end, a hollow center throughout its length, and an open ended slot on the entire length of its side. Part 20 is the slotted hollow axle, which screws into the base of the tip, 126. Part 15 is the rotator that rotates upon the flat platform 125 of the tip base. Part 16 is the upper jaw. The lower jaw is an integral part of the rotator. The hollow center is for temporary trapping of a portion of the suture, and the slot of the side is provide entry and exit for the suture. Part 21 is the L-shaped connecting rod which is a flat structure, with its side arm installed proximally, and connected to the round gear rod 25. Part 22 is the screw that attaches the distal end of the connecting rod to the periphery of the driving spur gear. Part 23 is the screw that attaches the proximal end of the L-connecting rod to the gear rod. Part 24 is the socket that houses the ball attached to the rotator. Part 25 is the push/pull rod whose distal end is attached to the upper end of the socket, and whose proximal end is attached to the short connector. Part 14 is the large base of the tip.

Figure 24:
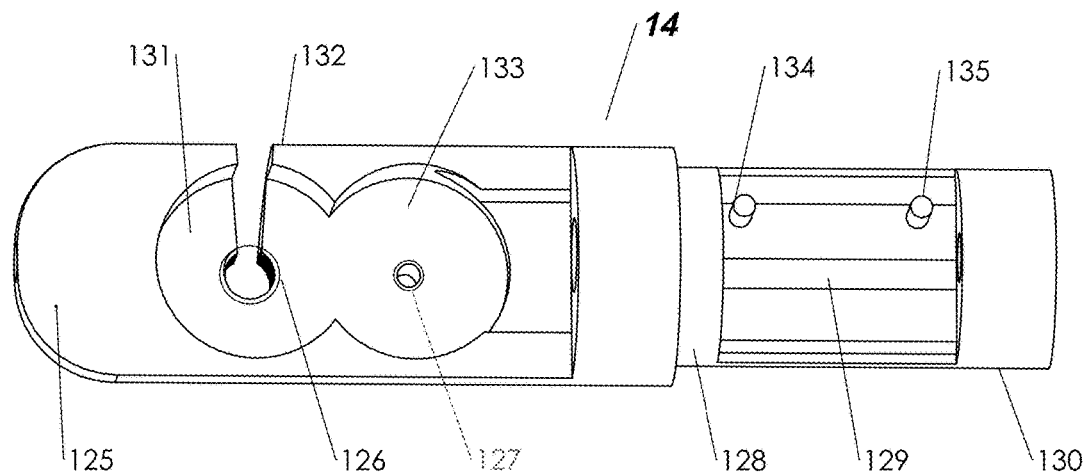
FIG. 24 is a top view of the tip-base.
Figure 25:
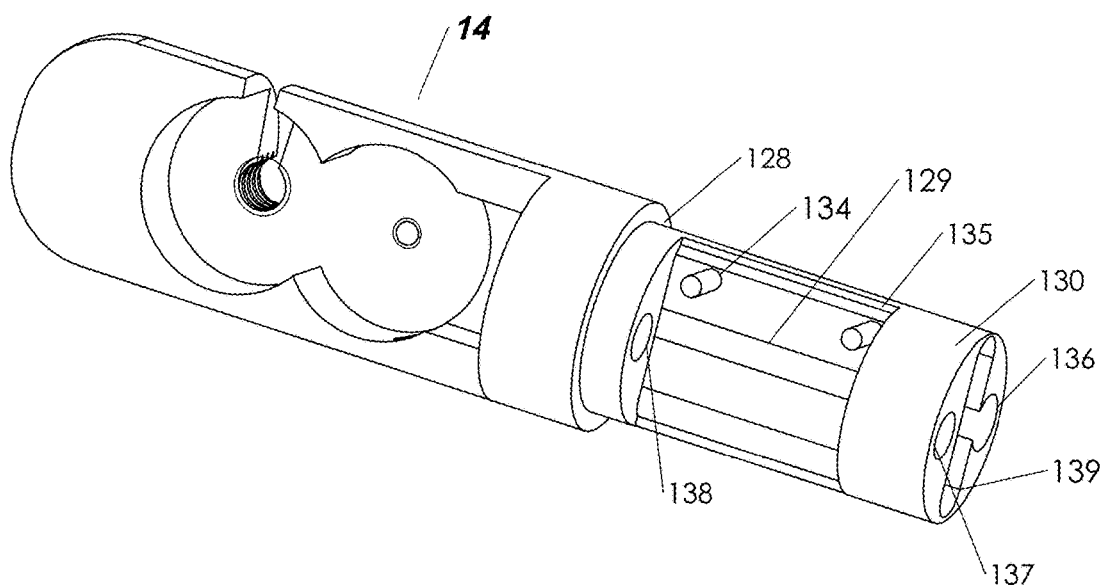
FIG. 25 is a perspective view of the tip-base.

Referring to FIG. 24 and FIG. 25, concerning the tip base, 126 is a female threaded hole that receives the male thread of the slotted hollow axle, 20 and illustrates element 130.

127 receives the mounting shoulder screw of the driving spur gear. 128 is a shoulder stop for the distal end of the sheath. 129 is the channel in which the gear rod 25 travels. 131 is the seat for the slotted driven spur gear. 132 is the v-shaped slot for the tail strand to slide in and out. 133 is the seat for the driving spur gear. 134 and 135 are the deflecting pillars, which are strategically located, so that they will deflect the distal end of the connecting rod off the dead center positions, just before the end of the travel of the side arm in either direction. 136 is the end of channel 129, for the gear rod to slide up and down. 137 and 138 are channels which guide the grasper rod. 139 is the end of an elliptical cut out which extends from the upper edge of the platform 125 to the upper end of the tip base. This space allows the L-shaped connecting rod to operate.

FIG. 26 is a perspective view of the slotted hollow axle, part 20 and illustrates element 140. 141 is the retaining flange. 142 is the hollow center. 143 is the open slot that extends through the entire length of the axle. 144 is the male thread. FIG. 27 shows one of the 3 pins that holds the slotted driven spur gear through 148 to underside of the rotator. FIG. 28 is a picture of the driven slotted spur gear. 145 shows the width of the gap between two adjacent teeth, which is vital for creating the slot 147. 146 is the central hole for mounting the part 20. FIG. 29 is a picture of the shoulder screw that holds the driving spur gear. FIG. 30 is a picture of the driving spur gear, showing the holes 149 and 150 for the mounting screw with counter-sunk head. 151 is a hole for a miniature screw that joins the driving spur gear to the hole 154 of the L-rod. FIG. 31 is a perspective view of the gear rod, which bears a female hole 152, on the side near its distal end, for attachment to 158 of the L-rod, and bears a female hole 153 on its proximal end for joining to the rod extension. FIG. 32 is a perspective view of the L-shaped connecting rod, whose proximal end 158 is attached to 152 of the gear rod, and whose distal end 154 is attached to 151 of the driving spur gear. 156 is the side arm, whose edges 155 and 157, make contact with the pillars 134 and 135.

Figure 37:
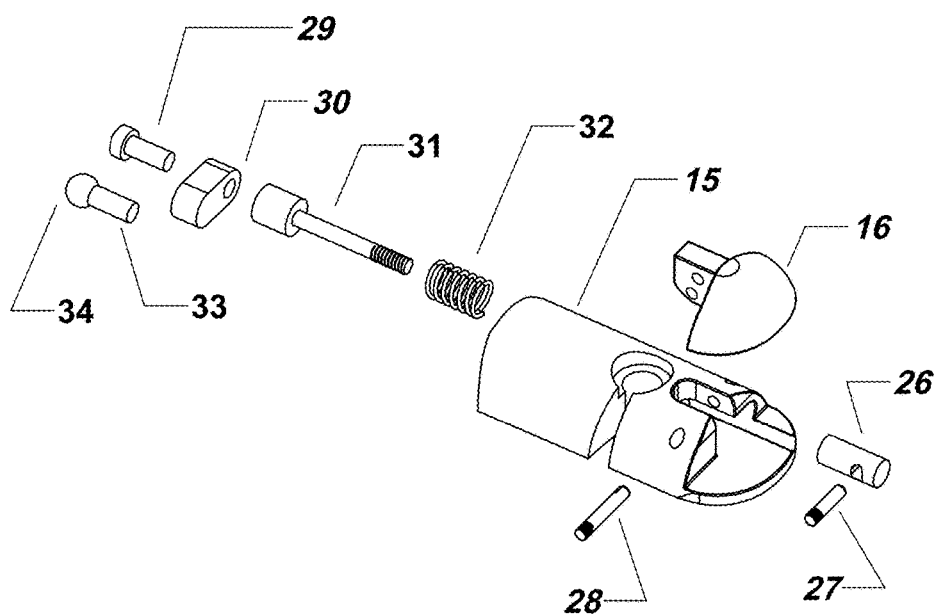
FIG. 37 is an exploded view of the same.

FIG. 37 is an exploded view of the rotator sub-assembly, showing the numerous components. Part 15 is the rotator. Part 16 is the upper jaw. Part 26 is the adaptor with an oval slot on its side for the pin 27 to move up and down, thereby converting vertical motion into horizontal, in moving the upper jaw. Part 27 is the pin that moves the upper jaw. Part 28 is the pin that acts as the fulcrum for moving the upper jaw. Part 29 is the screw that joins the oval plate to the plunger. Part 30 is the oval plate, which acts an adaptor which changes the line of action of the push/pull rod from the midline to the side of the rotator. Part 31 is the plunger, being part of the actuating system of the upper jaw. Part 32 is the compression spring. Part 33 is the stem of the ball. Part 34 is the ball. Part 35 is the socket. Part 36 are the 3 tiny pins for attaching the driven spur gear to the underside of the rotator.

Figure 38:
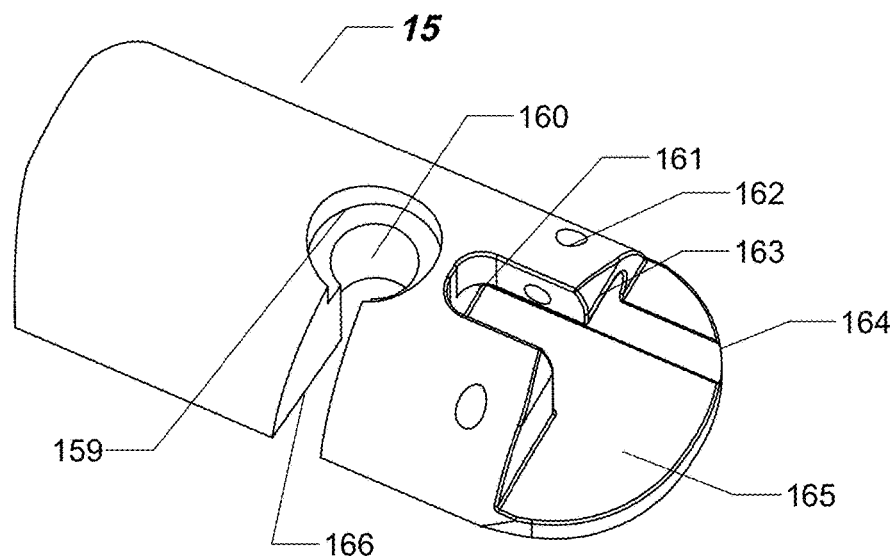
FIG. 38 is a perspective view of rotator itself, showing its front end.
Figure 39:
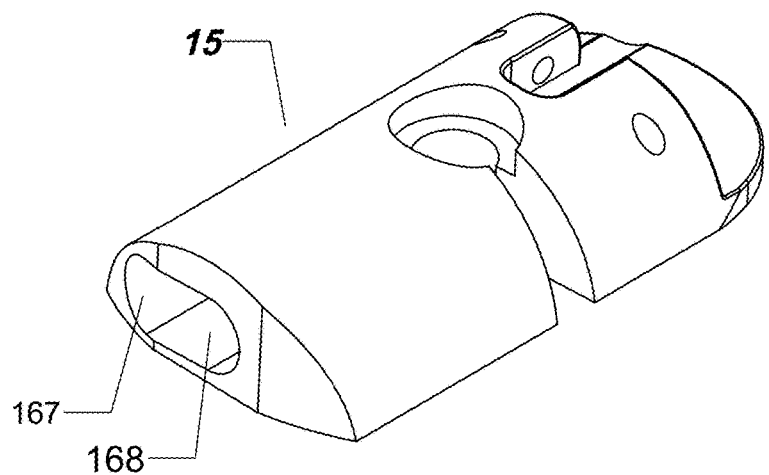
FIG. 39 is a perspective view of the same showing its rear end.

Referring to FIGS. 38 and 39, concerning the rotator itself, it is a complex and crucial structure. 160 is for the hollow axle, and 159 is for its counter-sunken flange. 161 is for the swinging arm of the upper jaw 173. 162 is for the fulcrum pin 28. 163 is the housing for the adaptor 26. 164 is an intentional groove on the lower jaw. 165 is the fixed lower jaw. 166 is the V-shaped slot for entry/exit of the tail strand of the suture. 167 is for installing the plunger and compression spring. The combination of 167 and 168 is for the oval plate.

FIG. 40 is a perspective view of the upper jaw, part 16. 169 is the hole for mounting the actuating pin 27, which moves the jaw. 170 is for mounting the screw 28 acting as fulcrum for the jaw. 171 is the gripping surface. 172 is the rounded upper surface.

Figures 43, 44:
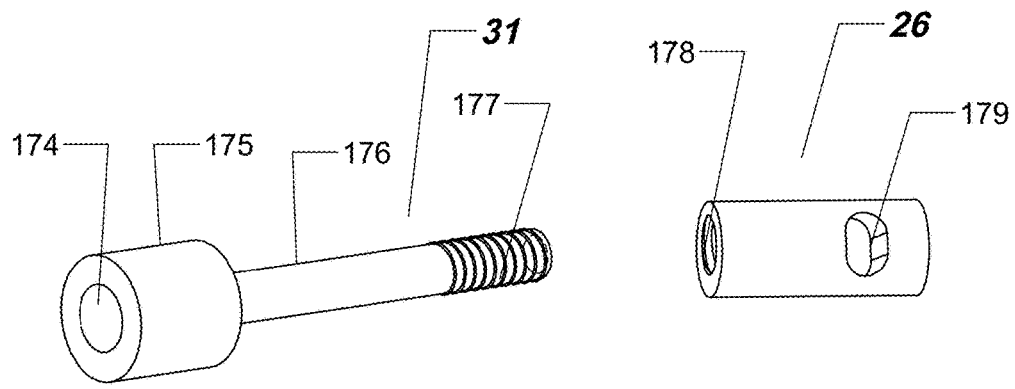
FIGS. 43, 44 and 45 show 3 of the components of the jaw sub-assembly that moves the upper jaw.

Referring to FIGS. 43 and 44, the top of the plunger has a female threaded hole 174 for the screw 29 that secures it to the oval plate. 175 is the head of plunger, and 176 is the shaft over which the compression spring rests. 177 is the male threaded end which mates into the female hole 178 on the adaptor 26. 179 is an oval slot transversely placed on the adaptor which is necessary to compensate for circular path of travel of pin 27 on the upper jaw.

Figure 45:
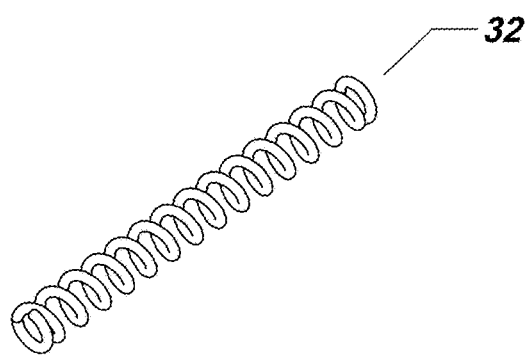

FIGS. 43, 44 and 45 show 3 of the components of the jaw sub-assembly that moves the upper jaw, including the plunger 31, the adaptor 26, and the compression spring 32.

Figure 46:
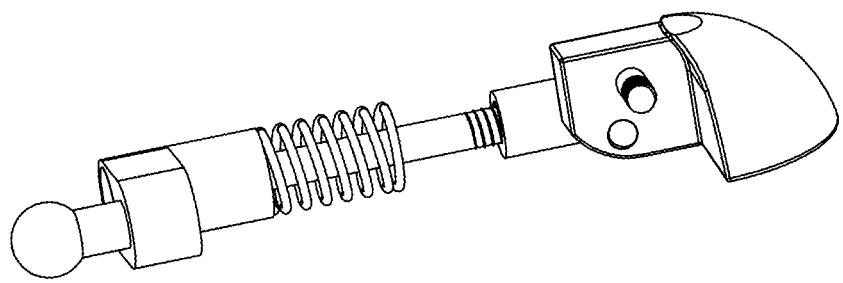
FIG. 46 is a side view of the entire jaw sub-assembly.
Figure 47:
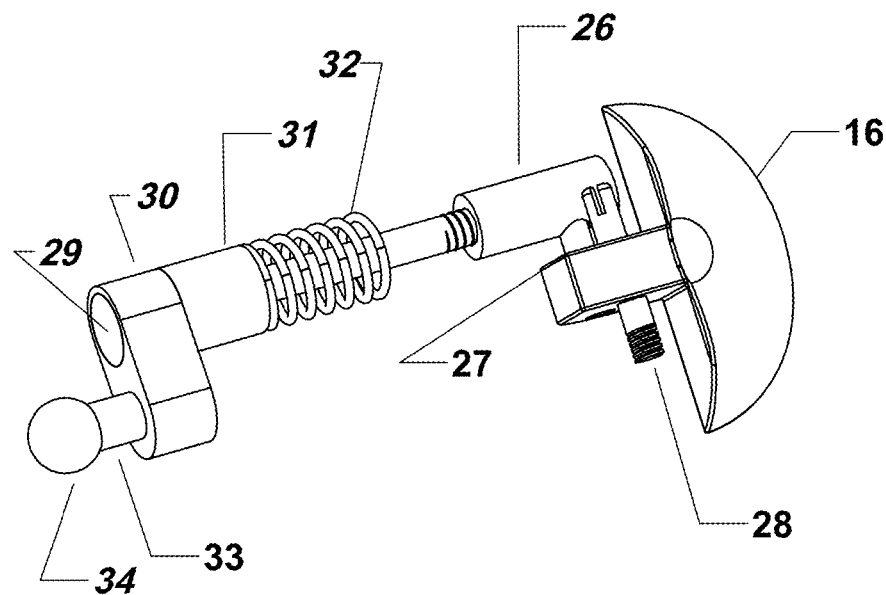
FIG. 47 is a top view of the jaw sub-assembly.
Figure 52:
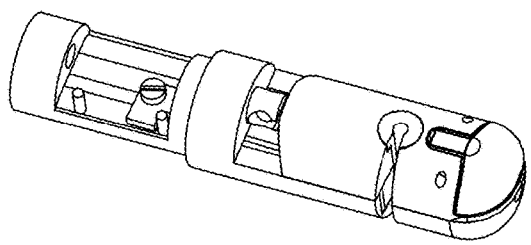
FIGS. 52, 53, 54, and 55, show the different positions of the rotator during its 360 degree rotation.
Figure 53:
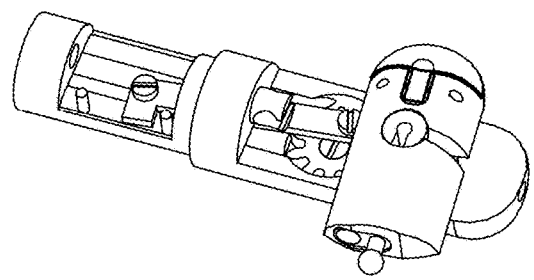
Figure 54:
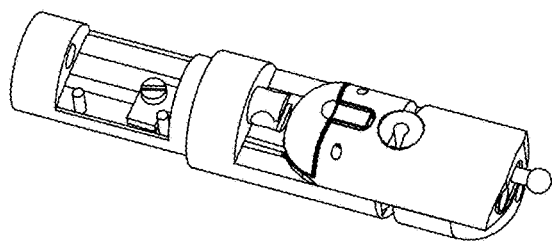

FIGS. 46 and 47 show the entire jaw sub-assembly. Part 26 is the adaptor with an oval slot placed horizontally on its side. Part 31 is the plunger which screws into the top of the adaptor 26, with a compression spring 32 mounted on its shaft. On its upper end is mounted the oval adaptor, secured with the screw 29. On the other end of the oval adaptor is mounted the stem of the ball, in the midline of the rotator, and in line with the socket.

FIG. 48 is a picture of the ball 34 with the stem 33. FIG. 49 is a perspective view of the oval plate located at the top of the rotator that is responsible for diverting the forces of actuation from the midline to the side of the rotator. 181 and 182 receives the counter-sunk screw. 180 receives the stem of the ball.

FIG. 50 and FIG. 51 are perspective views of the socket that contains the ball, illustrated by elements 183, 184. Note the socket is open at the lateral sides allowing the ball to escape and enter at the sides.

Figure 55:
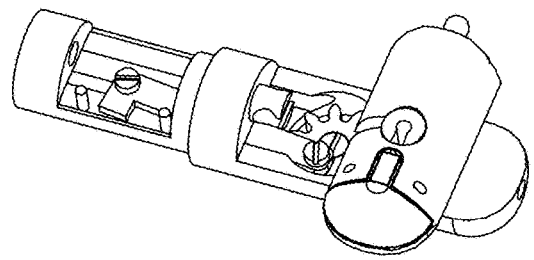

Referring to FIGS. 55, 57, and 58, the order of assembly is explained. First the sub-assemblies are constructed, which include the rotator sub-assembly, the tip-base sub-assembly, and the handle sub-assembly. Next the rotator sub-assembly is mounted on the tip-base sub-assembly. Then the two long operating rods are mounted followed by the outer sheath, and the proximal spacer. Next the rear end of this large sub-assembly is carefully inserted into the front of the handle, secured in place, followed by installation of the long and short connectors into the cavity in the handle, followed by installation of the triggers and compression springs.

FIG. 59 is diagram indicating the names of the different parts of a suture ligature, 1 for the head end, 2 the tail end, 3 the leading strand, and 4 the tail strand.

Figure 61:
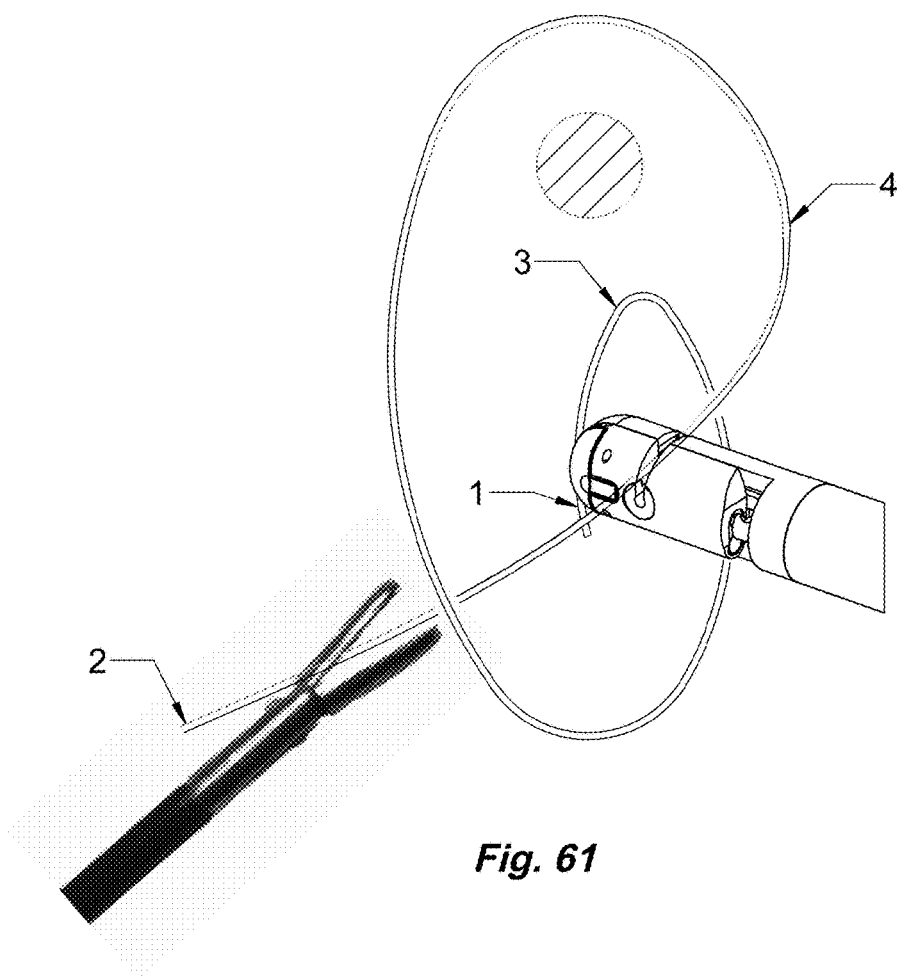
FIG. 61 is a diagram showing the current device being used in conjunction with a regular grasper to tie knot.

FIG. 61 shows how a knot is made using the present instrument. The tail end of the suture is grasped with a regular grasper, and is pulled taut so that the tail strand becomes relatively taut. The jaw of the mini-grasper then grasps the head end of the suture, and the instrument is pulled back over the tail strand, crossing it. The tail strand is then engaged in the V-slot on the upper surface of the tip of the present instrument, and seated firmly in the central space of the hollow axle. The rotation trigger 4, is then fired. The rotator will rotate through 180 degrees. Upon release of the rotation trigger, the compression spring will make the rotator rotate through the second 180 degrees, carrying the head end of the suture with it, producing the throw. Pulling the two ends apart will result in a knot. The process may be repeated.

What is claimed:

1. A laparoscopic instrument for intra-corporeal tying of knots with a free strand of a suture-ligature, comprising;
   a shaft attached to a handle with controls;
   a bullet shaped tip having a rotator subassembly, tip base subassembly and slider crank mechanism; wherein the rotator subassembly includes a slotted hollow axle with a hollow center and an open ended slot on its entire side, a mini-grasper with a movable jaw contained within the rotator subassembly and the rotator subassembly is configured to rotate 360 degrees on the hollow axle, along a sagittal plane of the long axis of the instrument; and wherein the mini-grasper is configured to grasp a head end of a suture, the slotted hollow axle is configured to temporarily trap a tail strand of the suture so that when the rotator subassembly rotates 360 degrees to form a knot in the suture.

2. A method of forming a laparoscopic knot with a free strand of a suture-ligature, comprising;

providing a laparoscopic instrument with a shaft attached to a handle with controls, a bullet shaped tip having a rotator subassembly, tip base subassembly and slider crank mechanism; wherein the rotator subassembly includes a slotted hollow axle with a hollow center and an open ended slot on its entire side, a mini-grasper with a movable jaw contained within the rotator subassembly and the rotator subassembly is configured to rotate 360 degrees on the hollow axle, along a sagittal plane of the long axis of the instrument;

grasping a head end of a suture with the mini-grasper, trapping a tail strand of the suture with the slotted hollow axle, forming a knot by rotating the rotator subassembly 360 degrees.

* * * * *